(12) United States Patent
Kanegae et al.

(10) Patent No.: US 11,730,397 B2
(45) Date of Patent: Aug. 22, 2023

(54) SIGNAL PROCESSING APPARATUS, SIGNAL PROCESSING SYSTEM, AND SIGNAL PROCESSING PROGRAM

(71) Applicant: HEALTH SENSING CO., LTD., Hachioji (JP)

(72) Inventors: Masatomo Kanegae, Hachioji (JP); Kyuichi Niizeki, Hachioji (JP)

(73) Assignee: HEALTH SENSING CO., LTD., Tokyo (JP)

( * ) Notice: Subject to any disclaimer, the term of this patent is extended or adjusted under 35 U.S.C. 154(b) by 145 days.

(21) Appl. No.: 17/613,362

(22) PCT Filed: May 6, 2021

(86) PCT No.: PCT/JP2021/018307
§ 371 (c)(1),
(2) Date: Nov. 22, 2021

(87) PCT Pub. No.: WO2022/176221
PCT Pub. Date: Aug. 25, 2022

(65) Prior Publication Data
US 2023/0086376 A1    Mar. 23, 2023

(30) Foreign Application Priority Data
Feb. 16, 2021 (JP) .................................. 2021-065009

(51) Int. Cl.
*A61B 5/11* (2006.01)
*A61B 5/352* (2021.01)

(52) U.S. Cl.
CPC ............ *A61B 5/1102* (2013.01); *A61B 5/352* (2021.01)

(58) Field of Classification Search
None
See application file for complete search history.

(56) References Cited

U.S. PATENT DOCUMENTS

| | | | |
|---|---|---|---|
| 5,941,837 A | 8/1999 | Amano et al. | |
| 2020/0138306 A1* | 5/2020 | Li | A61B 5/7267 |
| 2022/0323855 A1* | 10/2022 | Khare | A63F 13/216 |

FOREIGN PATENT DOCUMENTS

| | | |
|---|---|---|
| JP | H09-135819 A | 5/1997 |
| JP | H10-295657 A | 11/1998 |

(Continued)

OTHER PUBLICATIONS

PCT/ISA/210, 220, 237, "International Search Report for International Application No. PCT/JP2021/018307," dated Aug. 3, 2021.

(Continued)

*Primary Examiner* — Ankit D Tejani
(74) *Attorney, Agent, or Firm* — Manabu Kanesaka

(57) ABSTRACT

An apparatus yields signals that are equivalent to ECG signals and allow determination of a heartbeat interval or heart rate from bio-vibration signals including vibrations derived from heartbeats. An ECG meter acquires ECG signals of a sample, and a piezoelectric sensor acquires bio-vibration signals of the sample simultaneously. The bio-vibration signals include beating vibration signals derived from heartbeats. A learning unit of a prediction modeling apparatus establishes a prediction model by machine learning in which ECG signals are used as teaching data, and model input signals obtained by performing a specified processing on the bio-vibration signals are input. The learning unit delivers the prediction model to a prediction unit of a signal processing apparatus. The prediction model predicts and outputs pECG signals upon input of model input signals obtained by performing a specified processing on bio-vibration signals acquired from a subject under prediction with a piezoelectric sensor.

9 Claims, 10 Drawing Sheets

(56) References Cited

FOREIGN PATENT DOCUMENTS

| JP | 2012-65713 A | 4/2012 |
| JP | 2017-064338 A | 4/2017 |
| JP | 2018-082931 A | 5/2018 |
| JP | 2020-092738 A | 6/2020 |
| JP | 2020-188963 A | 11/2020 |

OTHER PUBLICATIONS

Kyuichi Niizeki, Biosystems Engineering, Graduate School of Science and Engineering, Yamagata University, Unrestrained measurement technologies for heartbeats and respiration and prediction of sleep condition, "Biological information sensing and application to prediction of human conditions" Chapter 2, Section 3, Technical Information Institute Co., Ltd. issued on Jul. 31, 2020, p. 145-152.

Mustafa Radha et al., Sleep stage Classification from Heart-rate Variability Using Long Short-term Memory Neural Network, Scientific Report, natureresearch, URL: https://doi.org/10.1038/s41598-019-49703-y.

* cited by examiner

Bio-vibration signals
Beating vibration signals
Differentiated bio-vibration signals Time (sec)
Model input signals Measured ECG pECG (bio-vibration signals)

pECG (beating vibration signals)

pECG (differentiated bio-vibration signals)

Time (sec)
ECG

Model input signals

ECG

Model input signals

ECG

Subject A under prediction

Subject B under prediction

Subject C under prediction

SIGNAL PROCESSING APPARATUS, SIGNAL PROCESSING SYSTEM, AND SIGNAL PROCESSING PROGRAM

TECHNICAL FIELD

The embodiments discussed herein are related to a signal processing apparatus, signal processing system, and signal processing program for outputting signals equivalent to ECG signals on the basis of bio-vibration signals that include vibration signals derived from heartbeats.

BACKGROUND ART

Existing piezoelectric sensors use a sheet-type piezoelectric element made of polyvinylidene difluoride (PVDF), a fluoride organic ferroelectric material. PVDF, a piezoelectric polymer material, produces electric polarization in response to increased displacement of ions arranged in crystal lattices by pressure or deformation. The piezoelectric element is horizontally placed between a positive electrode layer and a negative electrode layer. Current to voltage conversion of electric charges accumulated on the positive electrode layer and the negative electrode layer derives electric signals from the piezoelectric element.

This piezoelectric sensor, when placed on or under bedding such as bed mattress and futon, a seat of a chair, or other surfaces, or attached on a body surface such as the head, arm, or leg, detects bio-vibration signals. The detected bio-vibration signals are representative of vibrations derived from pulse waves (pressure pulse waves) or ballistocardiac movements, vibrations derived from respiratory, vibrations derived from body movements, vibrations derived from vocalization, and vibrations derived from snoring (see Non-Patent Literature 1, hereinafter referred to as NPTL1).

Nowadays, there are ongoing trials to acquire various information on a human body using neural networks.

For example, Patent Literature 1 describes a blood pressure prediction apparatus that predicts blood pressure using a Convolutional Neural Network (CNN). In addition, for example, NPTL2 describes a classification of sleep stages on the basis of heartbeat changes using a Long Short-Term Memory (LSTM) neural network.

CITATION LIST

Patent Literature

Patent Literature 1: Japanese Laid-open Patent Publication 2020-092738
NPTL1: Kyuichi Niizeki "Biological information sensing and application to prediction of human conditions, Chapter 2, Section 3 (unrestrained measurement technologies for heartbeats and respiration and prediction of sleep condition)" Technical Information Institute Co., Ltd. issued on Jul. 31, 2020; p. 145-152
NPTL2: Mustafa Radha, Pedro Fonseca, Arnaud Moreau, Marco Ross, Andreas Cerny, Peter Anderer, Xi Long & Ronald M. Aarts, "Sleep stage classification from heart-rate variability using long short-term memory neural networks", [online] Scientific Reports, [retrieved on 2021 Jan. 30]. Retrieved from the Internet: <URL: https://doi.org/10.1038/s41598-019-49703-y>

SUMMARY OF INVENTION

Technical Problem

Electrocardiogram (ECG) reflects electric activities of the heart, and from ECG signals, heartbeat interval and heart rate are determined. During an ECG measurement, electrodes of an ECG meter are kept attached on extremities or a chest. Any daily continuous ECG measurement, therefore, puts a substantial burden on a subject.

The piezoelectric sensor, on the other hand, for example, when placed on a bed or a chair, acquires the bio-vibration signals from the subject in a non-restraint manner. In addition, the piezoelectric sensor, for example, when integrated into a wristband, belt, watch, ring, headband, or other accessories and attached to the subject, acquires the bio-vibration signals as well. Acquisition of the bio-vibration signals with the piezoelectric sensor, therefore, hardly involves the burden on the subject. The bio-vibration signals acquired with the piezoelectric sensor include vibration signals derived from pulse waves (pressure pulse waves) and ballistocardiac movements.

The pulse waves and ballistocardiac movements are derived from the heartbeats, but their waveforms are not as sharp as waveforms of R-waves in an ECG. There are several known methods to determine heartbeat intervals from signals derived from the pulse wave and ballistocardiac movements. In a method, for example, the signals derived from the pulse wave or ballistocardiac movements are subjected to full-wave rectification integration, and subsequently obtained changes in an instantaneous phase lead to determination of heartbeat intervals. The conventional methods, however, have difficulties in determining the heartbeat interval or heart rate from the signals from the pulse waves or ballistocardiac movements because the waveforms are occasionally disturbed depending on a position of the piezoelectric sensor or a subject.

Accordingly, it is an object in one aspect of the embodiments to provide a signal processing apparatus, signal processing system, and signal processing program that output the signals that are on the basis of the bio-vibration signals including vibration signals derived from the heartbeats, are equivalent to the ECG signals, and facilitate determination of the heartbeat interval and heart rate.

Solution to Problem

To achieve the said object, the signal processing apparatus of the embodiments is provided with the following functions:

A prediction model established by machine learning in which ECG signals of a sample acquired with the ECG meter are used as teaching data, and model input signals obtained by performing a specified processing on the bio-vibration signals of the same sample including beating vibration signals derived from the heartbeats, simultaneously acquired with a bio-vibration signal acquisition apparatus, are input; and a prediction unit that outputs ECG-equivalent signals predicted by the said prediction model, referred to as pECG signals, upon input of the model input signals obtained by performing the said specified processing on the bio-vibration signals of a subject under prediction acquired with the said bio-vibration signal acquisition apparatus.

Preferably, the signal processing apparatus of the embodiments is provided with: The said bio-vibration signals, differentiated signals of the said bio-vibration signals, beating vibration signals extracted from the said bio-vibration signals, or differentiated signals of the said beating vibration signals, or absolutized signals of any of the said signals.

Preferably, the signal processing apparatus of the embodiments is provided with: The said specified processing that performs any of the following initial procedures in which the said bio-vibration signals are passed, in which the said bio-vibration signals are passed through a high-pass filter with a cutoff frequency of 0.5 Hz, in which the said bio-vibration signals are passed through a high-pass filter with a cutoff frequency appropriate for extraction of heart sound signals, and in which the said bio-vibration signals are passed through a band-pass filter (BPF) with a pass-band of 0.5 Hz to 40 Hz; either differentiation or absolutization, or both of the passed signals; and finally normalization of the calculated signals.

Preferably, the signal processing apparatus of the embodiments is provided with: The cutoff frequency of the high-pass filter appropriate for extraction of the heart sound signals from the said bio-vibration signals is 20 Hz to 40 Hz.

Preferably, the signal processing apparatus of the embodiments is provided with: A post-processing unit that eliminates a part of heartbeat data involving an outlying heartbeat, if found after heartbeat intervals are determined on the basis of the pECG signals output by the said prediction unit.

Preferably, the signal processing apparatus of the embodiments is provided with: The said bio-vibration signal acquisition apparatus that is a piezoelectric sensor.

Preferably, the signal processing apparatus of the embodiments is provided with: The said bio-vibration signal acquisition apparatus that is an accelerometry sensor.

Preferably, the signal processing apparatus of the embodiments is provided with: The said bio-vibration signal acquisition apparatus that is a piezoelectric sphygmometer or photoplethysmography (PPG).

Preferably, the signal processing apparatus of the embodiments is provided with: The said bio-vibration signal acquisition apparatus that is a phonocardiograph.

The signal processing system of the embodiments is provided with:

The said signal processing apparatus,

An ECG meter that acquires the ECG signals of the said sample,

The bio-vibration signal acquisition apparatus that acquires the bio-vibration signals from the said sample and subject under prediction, The prediction modeling apparatus with a learning unit that establishes the said prediction model by using the ECG signals of a sample acquired with the said ECG meter as the teaching data; and by inputting the model input signals obtained by performing the said specified processing on the bio-vibration signals of the same sample which are acquired with the said bio-vibration signal acquisition apparatus simultaneously with the said ECG signals and include the beating vibration signals derived from the heartbeats.

In addition, the signal processing program of the embodiments is provided with: A computer that has a prediction model established by the machine learning in which ECG signals of a sample acquired with the ECG meter are used as teaching data, and model input signals obtained by performing a specified processing on the bio-vibration signals of the same sample which are acquired with the bio-vibration signal acquisition apparatus simultaneously with the said ECG signals and include the beating vibration signals derived from the heartbeats; and functions as a prediction means that outputs the pECG signals predicted by the said prediction model upon input of the model input signals obtained by performing the said specified processing on the bio-vibration signals acquired from a subject under prediction with the said bio-vibration signal acquisition apparatus.

Advantageous Effects of Invention

According to the embodiments, an advantageous effect is to generate signals that are on the basis of the bio-vibration signals including vibration signals derived from the heartbeats, are equivalent to the ECG signals, and facilitate determination of the heartbeat interval and heart rate.

BRIEF DESCRIPTION OF DRAWINGS

FIG. 3(A) illustrates the model input signals of Subject A under prediction. FIG. 3(B) illustrates the measured ECG signals and pECG signals of Subject A under prediction as waveforms.

FIG. 5(A) illustrates the model input signals of Subject B under prediction. FIG. 5(B) illustrates the measured ECG signals and pECG signals of Subject B under prediction as waveforms.

FIG. 7(A) illustrates the model input signals of Subject C under prediction. FIG. 7(B) illustrates the measured ECG signals and pECG signals of Subject C under prediction as waveforms.

DESCRIPTION OF EMBODIMENTS

Pulse waves (pressure pulse waves) and ballistocardiac movements detected by a piezoelectric sensor are derived from vibrations of the heart (heartbeats). The pulse waves are generated by arterial pulsations that are transmitted through the vascular wall and reflect systolic and diastolic movements of a blood vessel. The ballistocardiac movements, on the other hand, reflect vibrations that are generated from the heart and transmitted through the body surface and tissues in the body. The piezoelectric sensor, accordingly, when closely attached to the body surface said an artery such as the superficial temporal artery, brachial artery, or radial artery for measurement, detects pressure pulse waves. On the other hand, the piezoelectric sensor, when attached on the body surface not said the artery or placed, for example, under the bedding, detects ballistocardiac movements. In this description, vibrations derived from the pulse waves and/or vibrations derived from the ballistocardiac movements are collectively referred to as beating vibrations. In addition, waveforms representative of beating vibrations are referred to as beating vibration waveforms, and signals representative of beating vibrations are referred to as beating vibration signals.

Hereinafter, a signal processing system according to the embodiments is described in detail with reference to the accompanying drawings. Common components in all the drawings describing the embodiments are given the same sign, and thereafter repeated explanations are omitted.

Firstly, an idea driving the present inventors to achieve the embodiments is explained.

An electrocardiogram (ECG) represents electric activities of the heart, and the beating vibrations are derived from beating of the heart. Both signals of the ECG (hereinafter referred to as ECG signals) and beating vibration signals are generated in association with systolic and diastolic movements of the heart. ECG waveforms, therefore, are considered correlative to beating vibration waveforms. The inventors of the embodiments have projected a model that predicts and outputs ECG signals equivalent to the ECG signals in an unspecified human in response to input of beating vibration signals in the human. The model is projected to be established by machine learning performed with multiple datasets each including beating vibration signals acquired from a human and ECG signals from the same human as input data and teaching data, respectively. Hereinafter, an ECG predicted by this prediction model and the signals analogous to ECG signals are referred to as predicted ECG (pECG) and predicted ECG signals, respectively.

Figure 1:
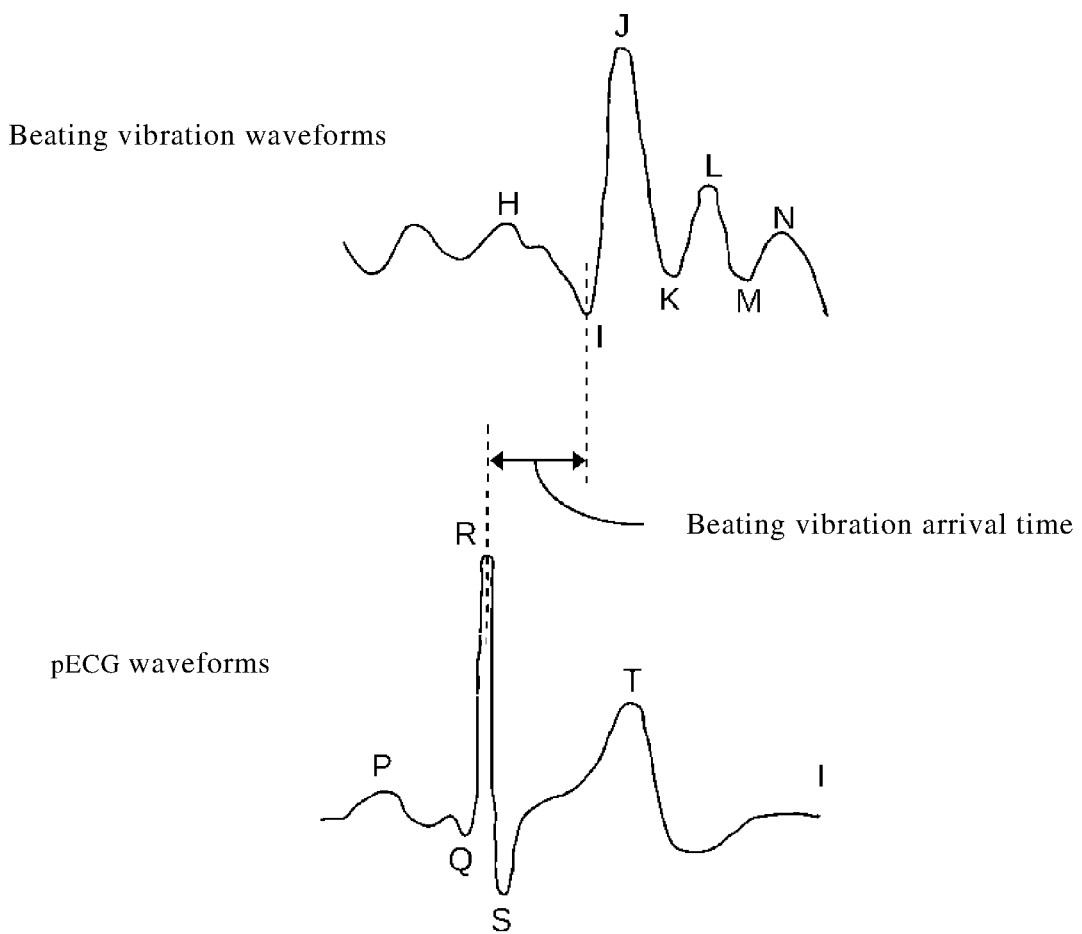
FIG. 1 The figure illustrates an example of beating vibrations and pECG as waveforms.

Now refer to FIG. 1. During a process from a left ventricular electric excitation (R wave in the ECG) to ejection of blood into an aorta by ventricular contraction, a vibration is generated. The vibration takes some time to reach the piezoelectric sensor. This time interval for pulse waves is referred to as pulse arrival time (PAT) The PAT, for example, represents a time interval from a R-wave peak in an ECG to a rising of the pulse wave at a measurement point. In the embodiments, the time interval needed for the cardiac vibration including the ballistocardiac movement to reach the piezoelectric sensor is defined as a beating vibration arrival time, and thereby information corresponding to the PAT can be obtained. Specifically, for example, the beating vibration arrival time is a time interval from the R-wave peak in the ECG to a rising of a beating vibration waveform obtained at the measurement point with the piezoelectric sensor.

The rising of the beating vibration waveform, accordingly, is delayed only by the beating vibration arrival time from the R-wave in the ECG. In a process of machine learning, however, the time of the R-wave in the ECG and time of the rising of the beating vibration waveform are reflected in the prediction model. The inventors of the embodiments predicted that the R-wave in the pECG (hereinafter, referred to as predicted R-wave) would not occur at the time of the rising of the beating vibration waveform and, as illustrated in FIG. 1, would precede the concerned rising only by the beating vibration arrival time. Specifically, the inventors of the embodiments presumed that the predicted R-wave would appear in the pECG at the time when the measured R-wave would appear in the ECG obtained with an electrocardiograph (ECG meter).

Figure 2:
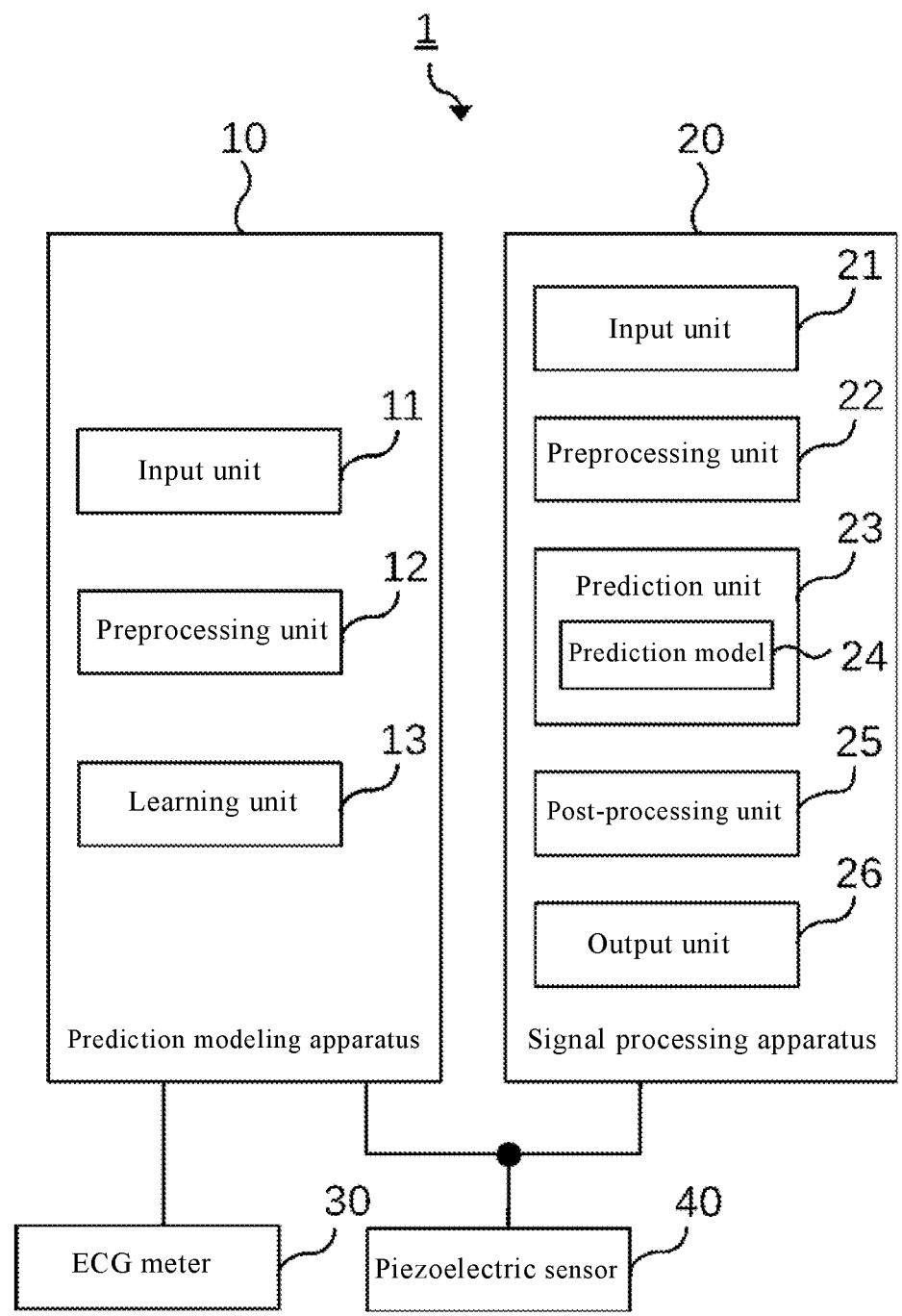
FIG. 2 The figure illustrates an example of the signal processing system according to the embodiments.

FIG. 2 illustrates an example of configuration of a signal processing system 1 according to the embodiments.

The signal processing system 1 includes a prediction modeling apparatus 10, a signal processing apparatus 20, an ECG meter 30, and a piezoelectric sensor 40. The prediction modeling apparatus 10 is connected with the ECG meter 30 and piezoelectric sensor 40 wired or wirelessly. The prediction modeling apparatus 10 may be connected with the ECG meter 30 and/or the piezoelectric sensor 40 through a network.

The signal processing apparatus 20 is connected with the piezoelectric sensor 40 in a wire or wireless mode. The signal processing apparatus 20 may be connected with the piezoelectric sensor 40 through a network.

The prediction modeling apparatus 10 is connected to the signal processing apparatus 20 wired or wirelessly. The prediction modeling apparatus 10 may be connected with the signal processing apparatus 20 through a network. The prediction modeling apparatus 10 and signal processing apparatus 20 may be integrated into one apparatus.

The prediction modeling apparatus 10 is equipped with a central processing unit (CPU), main memory including random access memory (RAM) and others as well as a memory unit including a hard disk and others. The prediction modeling apparatus 10 can be implemented with a computer. The prediction modeling apparatus 10, for example, can be implemented with a server, personal computer (PC), tablet PC, smart phone, or other devices. In addition, the prediction modeling apparatus 10, for example, can be implemented in cloud computing. The memory unit in the prediction modeling apparatus 10 stores a prediction modeling program. The CPU in the prediction modeling apparatus 10 reads the prediction modeling program from the memory unit into the main memory and executes the program, thereby realizing functions each of an input unit 11, a preprocessing unit 12, and a learning unit 13.

The signal processing apparatus 20 is equipped with CPU, main memory including random access memory (RAM) and others as well as a memory unit including a hard disk and others. The signal processing apparatus 20 can be implemented with the computer. The signal processing apparatus 20, for example, can be implemented with a server, PC, tablet PC, smart phone, or other devices. In addition, the signal processing apparatus 20, for example, can be implemented in cloud computing.

The memory unit in the signal processing apparatus 20 stores a signal processing program. The CPU in the signal processing apparatus 20 reads the signal processing program from the memory unit into the main memory and executes the program, thereby realizing functions each of an input unit 21, preprocessing unit 22, prediction unit 23, post-processing unit 25, and output unit 26. The prediction unit 23 has a prediction model 24. As described below, the prediction model 24 is established by the learning unit 13 in the prediction modeling apparatus 10. The prediction modeling apparatus 10 and signal processing apparatus 20 can be implemented with the same computer. The prediction modeling apparatus 10 and signal processing apparatus 20, for example, can be implemented with the same server, PC, tablet PC, smart phone, or other devices.

The ECG meter 30 acquires ECG from a human or animal.

The piezoelectric sensor 40, for example, is a piezoelectric sensor that uses a sheet-type piezoelectric element made of polyvinylidene difluoride (PVDF). The piezoelectric sensor 40 acquires bio-vibrations from a human or animal. The detected bio-vibrations are derived from heartbeats and also include beating vibrations transmitted from the heart to the piezoelectric sensor 40. The beating vibration signals are signals representative of pulse waves (pressure pulse waves) and vibrations generated by ballistocardiac movements. The bio-vibrations additionally include vibrations generated by respiration, body movements, vocalization, and snoring.

The sheet-type piezoelectric sensor 40 can be placed on or under bedding such as bed mattress and futon, seat of a chair, and other surfaces. The piezoelectric sensor 40 can be integrated into a wristband, belt, watch, ring, or headband to be attached closely to the body surface of a human head, finger, arm, leg, or other part. That is, the piezoelectric sensor 40 acquires bio-vibrations at a specified point of the human or animal.

The piezoelectric sensor 40 is an example of a bio-vibration signal acquisition apparatus of the embodiments.

Then, the prediction modeling apparatus 10 is described for each unit in details. Administrators, etc. of the prediction modeling apparatus 10 simultaneously acquire ECG from a sample using the ECG meter 30 and bio-vibration data from the sample using the piezoelectric sensor 40.

In this connection, the sample is a human or animal. The sample includes at least 1 human or animal.

The said simultaneous acquisition is achieved by a session in which measurements of ECG signals and bio-vibration signals are started and finished at the same time. The simultaneous acquisition of the ECG signals and bio-vibration signals allows learning how to correct time differences between ECG signals and bio-vibration signals or beating vibration signals, that is, to improve a correlation between the ECG signals and bio-vibration signals or beating vibration signals, thereby leading to establishment of the prediction model capable of presenting pECG finely.

The input unit 11 receives the ECG signals of each sample from the ECG meter 30. In addition, the input unit 11 receives the bio-vibration signals of each sample from the piezoelectric sensor 40. The input unit 11 transfers the received ECG signals and bio-vibration signals to the preprocessing unit 12. The input unit 11 may temporarily store the ECG signals and bio-vibration signals in the memory unit of the prediction modeling apparatus 10, and read the ECG signals and bio-vibration signals from the memory unit and transfer these signals to the preprocessing unit 12 when the learning unit 13 directs the prediction model 24 to perform machine learning.

The preprocessing unit 12 applies a specified processing, explained below, to bio-vibration signals to generate model input signals and transfers the generated model input signals to the learning unit 13.

For example, the preprocessing unit 12 transfers the bio-vibration signals themselves to the learning unit 13 as the model input signals.

Or, for example, the preprocessing unit 12 differentiates the bio-vibration signals. Then, the preprocessing unit 12 transfers differentiated bio-vibration signals to the learning unit 13 as the model input signals.

In addition, the bio-vibration signals include signals representative of vibrations derived from heartbeats (beating vibration signals), vibrations derived from respiratory, vibrations derived from body movements, vibrations derived from vocalization, and vibrations derived from snoring. For example, the preprocessing unit 12 passes the bio-vibration signals through a high-pass filter with a cutoff frequency of 0.5 Hz, a high-pass filter with the cutoff frequency (20 Hz to 40 Hz) appropriate for extraction of heart sound signals from the said bio-vibration signals, or a band-pass filter (BPF) with a pass-band of 0.5 Hz to 40 Hz to isolate or extract the beating vibration signals. By this way, the preprocessing unit 12 extracts the beating vibration signals from the bio-vibration signals and transfers the extracted beating vibration signals to the learning unit 13 as the model input signals.

Or, for example, the preprocessing unit 12 performs either or both of differentiation and absolutization of the beating vibration signals extracted from the bio-vibration signals. Then, the preprocessing unit 12 transfers these processed signals to the learning unit 13 as the model input signals.

Examples of the model input signals in the embodiments are the bio-vibration signals themselves, the differentiated bio-vibration signals, the beating vibration signals extracted from the bio-vibration signals, differentiated beating vibration signals, and absolutized signals of the beating vibration signals or differentiated beating vibration signals. The model input signals may be the other beating vibration signals generated by the specified processing of the bio-vibration signals.

ECG signals and the model input signals transferred to the learning unit 13 are desirably normalized. The preprocessing unit 12 calculates a ratio of a deviation from the mean of all data on the ECG signals acquired for a specified interval (30 seconds, for example) with respect to a standard deviation (each value of the ECG signals—the mean)/standard deviation) for normalization. In the same manner, the preprocessing unit 12 calculates the ratio of the deviation from the mean of all data on the model input signals acquired for the specified interval (30 seconds, for example) with respect to the standard deviation (each value of the input signals—the mean)/standard deviation) for normalization. By using normalized ECG signals and model input signals, individual differences of samples or prediction subjects are cancelled, increasing versatility of the prediction model 24 and also improving accuracy in prediction.

Normalization, however, precludes a prediction unit 23, described below, from predicting ECG on a real-time basis. For this reason, the preprocessing unit 12 may transfer the non-normalized ECG signals and model input signals to the learning unit 13, and the learning unit 13 may perform machine learning with the said model input signals using the said ECG signals as the teaching data to establish the prediction model 24.

After receiving the ECG signals and model input signals of each sample from the preprocessing unit 12, the learning unit 13 performs machine learning with the model input signals using the ECG signals of each sample as the teaching data to establish the prediction model 24.

When the machine learning is completed, the learning unit 13 transfers the prediction model 24 to the prediction unit 23 in the signal processing apparatus 20.

Examples of neural network used for machine learning include Convolutional Neural Network (CNN), Recurrent Neural Network (RNN), and Long Short-Term Memory (LSTM) neural network. To capture long-term trends of ECG signals and bio-vibration signals, neural networks involving recurrent connections (RNN and LSTM) are desirable.

Then, the signal processing apparatus 20 is described for each unit in details. The input unit 21 receives bio-vibration signals of a prediction subject from the piezoelectric sensor 40 and transfers the bio-vibration signals to the preprocessing unit 22. The prediction subject is human if the sample is human or animal if the sample is animal.

After receiving the bio-vibration signals from the input unit 21, the preprocessing unit 22 performs the same processing on the bio-vibration signals as that performed by the preprocessing unit 12 to generate input signals and then transfers the input signals to the prediction unit 23.

For example, the preprocessing unit 22 transfers the bio-vibration signals themselves to the prediction unit 23 as the model input signals.

Or, for example, the preprocessing unit 22 differentiates the bio-vibration signals. Then, the preprocessing unit 22 transfers differentiated bio-vibration signals to the prediction unit 23 as the model input signals.

For example, the preprocessing unit 22 passes the bio-vibration signals through a high-pass filter with a cutoff frequency of 0.5 Hz, a high-pass filter with the cutoff frequency (20 Hz to 40 Hz) appropriate for extraction of heart sound signals from the said bio-vibration signals, or a band-pass filter (BPF) with a pass-band of 0.5 Hz to 40 Hz to extract the beating vibration signals. Then, the preprocessing unit 22 transfers the beating vibration signals to the prediction unit 23 as the model input signals.

Or, for example, the preprocessing unit 22 extracts the beating vibration signals from the bio-vibration signals and performs either or both of differentiation and absolutization of the extracted beating vibration signals. Then, the preprocessing unit 22 transfers these processed signals to the learning unit 13 as the model input signals.

Example of the model input signals in the embodiments are the absolutized bio-vibration signals themselves, the differentiated bio-vibration signals, the beating vibration signals extracted from the bio-vibration signals, or the differentiated beating vibration signals. The model input signals may be the other beating vibration signals generated by the specified processing of the bio-vibration signals.

As with learning, it is desirable to normalize the model input signals before transferring to the prediction unit 23.

After receiving the model input signals from the preprocessing unit 22, the prediction unit 23 inputs the model input signals in the prediction model 24. In response to input of the model input signals, the prediction model 24 performs calculation to determine an ECG condition of the highest likelihood. After calculation, the prediction model 24 determines pECG as the ECG condition of the highest likelihood and outputs the predicated pECG signals to the post-processing unit 25. The pECG signals are equivalent to ECG signals, and their waveforms include at least predicated R-waves (hereinafter, referred to as predicted R-waves). On the basis of the predicted R-wave, therefore, heartbeat intervals and heart rates can be determined.

In the pECG, the predicted heartbeat interval is found to be an outlier (for example, an adjacent predicted R-wave interval is found too long or too short). The post-processing unit 25, for example, checks whether the concerned outlier is attributable to wrong prediction in the prediction model 24 or not, by referring to heartbeat intervals in the ECG of a sample used for learning in the prediction model 24. For example, the post-processing unit 25 may judge whether the heartbeat interval predicted on the basis of normal heartbeat interval values is normal or outlying and eliminate a part of heartbeat data involving outliers, if judges so, as post-processing.

On the other hand, the post-processing may be omitted, for example, when the embodiments are implemented in an application filed where humans are able to judge whether the outlier heartbeats are attributable to wrong prediction of the prediction model 24 or not, by checking presented heartbeat intervals.

The output unit 26 presents pECG signals output by the post-processing unit 25 on a display of the signal processing apparatus 20, records the pECG signals in a memory unit of the signal processing apparatus 20, and send the pECG signals to a terminal owned by the administrator of the signal processing apparatus 20.

Example 1

The inventors of the embodiments conduct a verification experiment using 13 humans as subjects. In the verification experiment, a seat cushion with the piezoelectric sensor 40 attached is placed on a seat of a chair. Electrodes for ECG are attached to the chest of each subject to acquire ECG signals of each subject with the ECG meter 30 through bipolar leads. At the same time of acquisition of the ECG signals, bio-vibration signals on the buttock of each subject who sits on the chair are acquired through the piezoelectric sensor 40. A measurement time is 30 seconds for each subject.

The learning unit 13 assigns the prediction model 24 to machine learning by a leave-one-out procedure. The neural network used is bidirectional LSTM (BiLSTM) neural network that transfers the learning data to a bidirectional long short-term memory layer.

More specifically, ECG signals acquired for 30 seconds from each of 13 subjects are firstly normalized by taking the ratio of the deviation from the mean of all data on the ECG signals with respect to the standard deviation ((each value of the ECG signals—the mean)/standard deviation). In the same manner, the ratio of the deviation from the mean of all data on the model input signals acquired for 30 seconds from each of 13 subjects with respect to the standard deviation ((each value of the model input signals—the mean)/standard deviation) is determined for normalization.

Then, for each subject under prediction, using the normalized model input signals and the normalized ECG signals (teaching signals) from the other 12 subjects (samples) as the training data, the prediction model 24 is generated based on the bidirectional LSTM neural network.

Then, the normalized model input signals from the subjects under prediction are input in the prediction model 24, and the prediction model 24 outputs pECG signals as the predicted ECG. The model input signals include 3 types of signals, bio-vibration signals themselves, beating vibration signals extracted by passing the bio-vibration signals through a 0.5 Hz high-pass filter, and differentiated bio-vibration signals.

In this verification experiment, however, pECG signals output by the prediction model 24 do not undergo post-processing.

The verification experiment results demonstrate that a predicted R-wave in pECG occurs almost simultaneously with a R-wave in measured ECG in all of 13 subjects (under prediction).

In this section below, the verification experiment results in 3 subjects (Subject A under prediction, Subject B under prediction, and Subject C under prediction) are explained by referring to FIGS. 3(A) to 8.

Figure 3A:
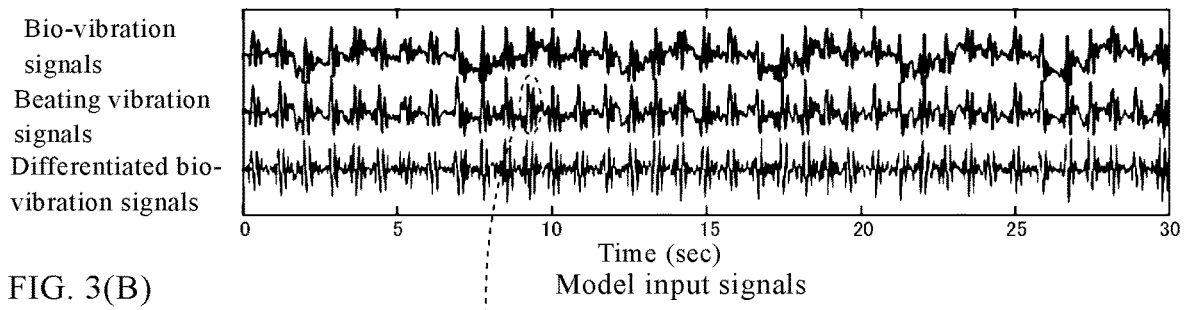
FIG. 3(A) and FIG. 3(B) The figures illustrate the model input signals of Subject A under prediction as well as the measured ECG signals and pECG signals of Subject A under prediction as waveforms.

FIG. 3(A) illustrates the model input signals of Subject A under prediction. The top tier illustrates bio-vibration signals as waveforms. The middle tier illustrates the beating vibration signals as waveforms. The bottom tier illustrates the differentiated bio-vibration signals as waveforms.

Figure 3B:
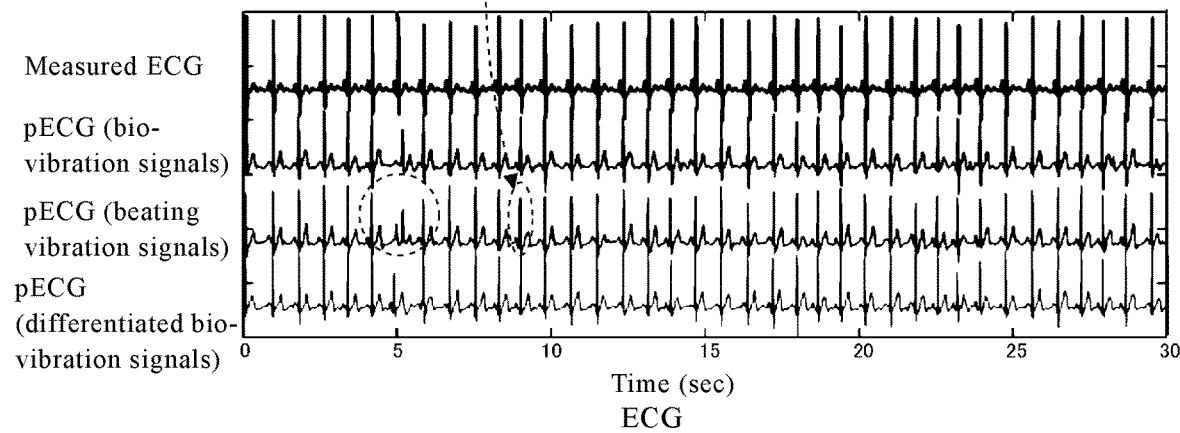

FIG. 3(B) illustrates the measured ECG signals and the pECG signals from Subject A under prediction as waveforms. The top tier illustrates the measured ECG signals as waveforms. The second tier from the top illustrates waveforms of the pECG signals output by the prediction model 24 on the basis of the bio-vibration signals, which are input in the prediction unit 23 as the model input signals. The third tier from the top illustrates waveforms of the pECG signals output by the prediction model 24 in response to the beating vibration signals, which are input in the prediction unit 23 as the model input signals. The bottom tier illustrates waveforms of the pECG signals output by the prediction model 24 in response to the differentiated bio-vibration signals, which are input in the prediction unit 23 as the model input signals.

As illustrated in FIG. 3(B), the predicted R-waves in each of 3 types of pECG patterns occurs almost simultaneously with the R-waves in the measured ECG. Especially, for example, as indicated with an arrow extending from FIG. 3(A) to FIG. 3(B), 2 adjacent peaks occur around 9 seconds in the model input signals (see the beating vibration signals), but it should be noted that only 1 predicted R-wave is presented in the pECG generated from the beating vibration signals.

Figure 4:
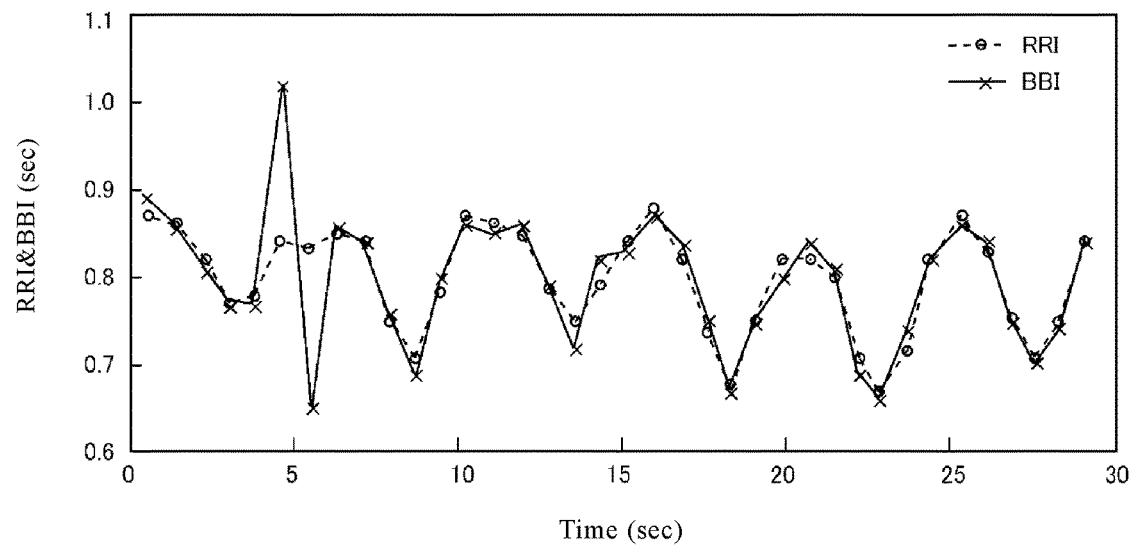
FIG. 4 The figure illustrates R-wave-based heartbeat intervals (RRIs) determined from the measured ECG signals and bio-vibration-based heartbeat intervals (BBIs) determined from the pECG on the basis of the beating vibration signals from Subject A under prediction, which are input as the model input signals.

FIG. 4 illustrates R-wave-based heartbeat intervals (R-wave-to-R-wave intervals, hereinafter referred to as RRIs) determined from the measured ECG signals and bio-vibration-based heartbeat intervals (bio-vibration-to-bio-vibration intervals, hereinafter referred to as BBIs) determined from the pECG on the basis of the beating vibration signals from Subject A under prediction, which are input as the model input signals.

As illustrated in FIG. 4, the RRIs and BBIs fluctuate in cycles of approximately 5 seconds, and the fluctuations occur in response to respirations. The heartbeat intervals, which are affected by respiratory activity, shortened during inhalation and prolonged during expiration. The heartbeat intervals fluctuate in cycles similar to respiratory patterns.

As illustrated in FIG. 3(B) and FIG. 4, for example, when the beating vibration signals are used as the model input signals, the BBIs (the predicted R-wave interval) around 5 seconds are markedly disturbed. As described said, a prediction error occurs in the pECG on rare occasion.

Figure 5A:
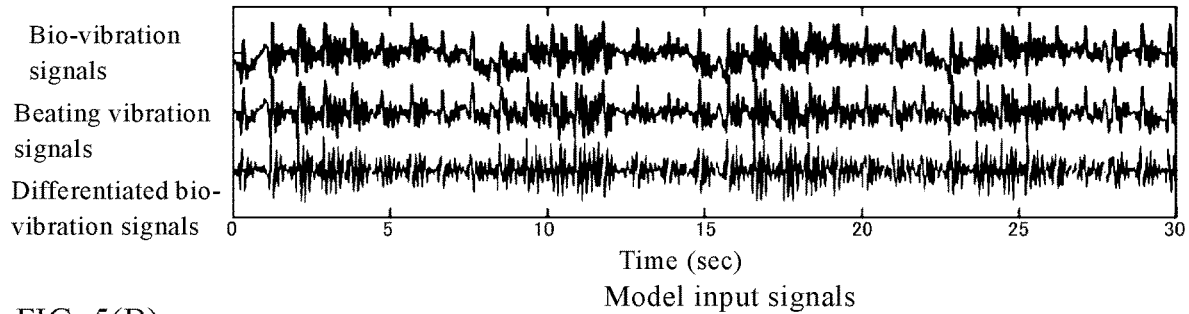
FIG. 5(A) and FIG. 5(B) The figures illustrate the model input signals of Subject B under prediction as well as the measured ECG signals and pECG signals of Subject B under prediction as waveforms.

FIG. 5(A) illustrates the model input signals of Subject B under prediction. As with FIG. 3(A), the top tier of FIG. 5(A) illustrates the bio-vibration signals as waveforms. The middle tier in FIG. 5(A) illustrates the beating vibration signals as waveforms. The bottom tier of FIG. 5(A) illustrates the differentiated bio-vibration signals as waveforms.

Figure 5B:
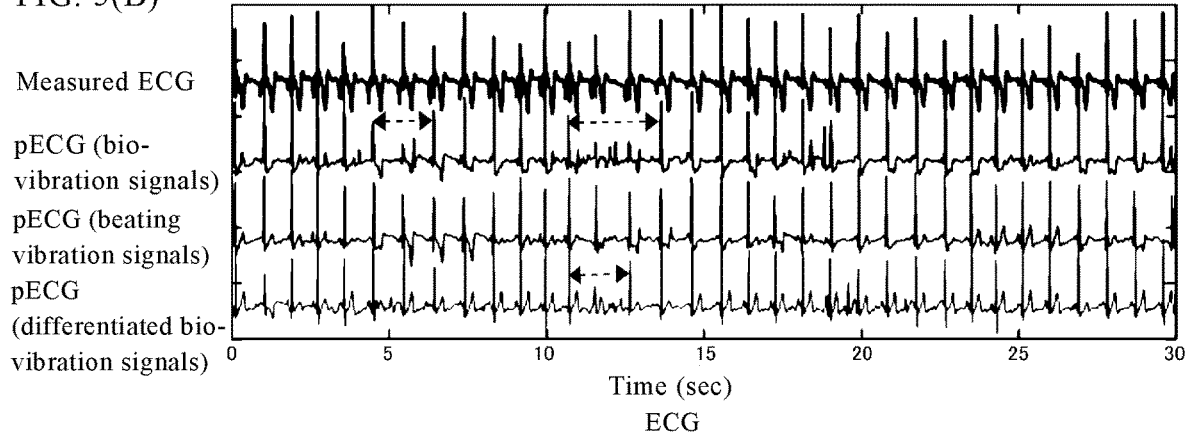

FIG. 5(B) illustrates the measured ECG signals and pECG signals of Subject B under prediction as waveforms. As with FIG. 3(B), the top tier of FIG. 5(B) illustrates the measured ECG signals as waveforms. The second tier from the top in FIG. 5(B) illustrates waveforms of the pECG signals output by the prediction model 24 on the basis of the bio-vibration signals, which are input in the prediction unit 23 as the model input signals. The third tier from the top of FIG. 5(B) illustrates waveforms of the pECG signals output by the prediction model 24 on the basis of the beating vibration signals, which are input in the prediction unit 23 as the model input signals. The bottom tier in FIG. 5(B) illustrates waveforms of the pECG signals output by the prediction model 24 on the basis of the differentiated bio-vibration signals, which are input in the prediction unit 23 as the model input signals.

Figure 6:
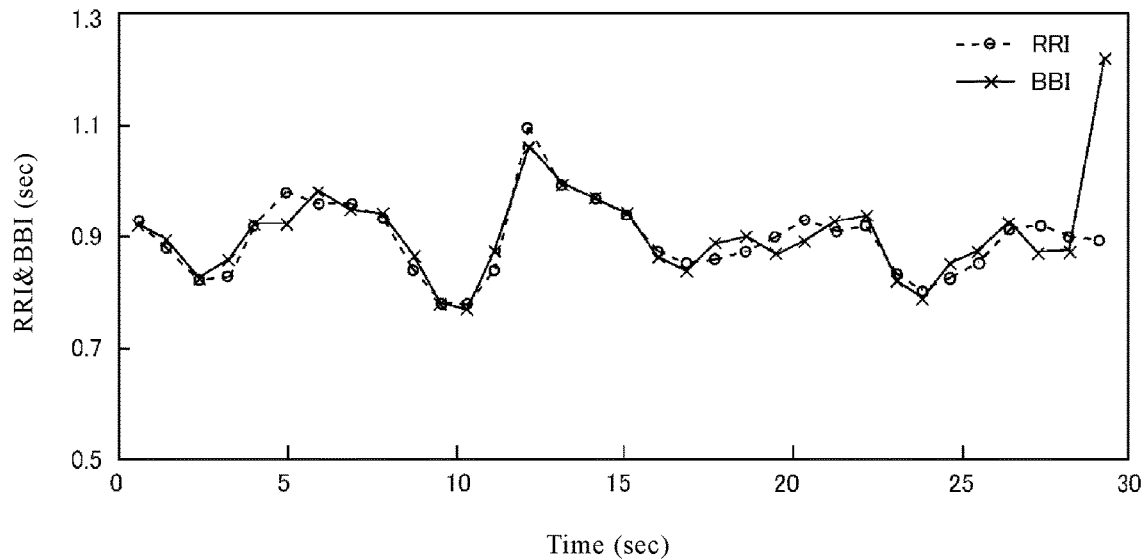
FIG. 6 The figure illustrates R-wave-based heartbeat intervals (RRIs) determined from the measured ECG signals and bio-vibration-based heartbeat intervals (BBIs) determined from the pECG on the basis of the beating vibration signals from Subject B under prediction, which are input as the model input signals.

FIG. 6 illustrates heartbeat intervals (RRIs) determined from the measured ECG signals and heartbeat intervals (BBIs) determined from the pECG on the basis of the beating vibration signals from Subject B under prediction, which are input as the model input signals.

In FIG. 5(B), the predicted R-wave is not presented in sections indicated with an arrow in the second tier from the top illustrating the pECG on the basis of the bio-vibration signals and in the bottom tier illustrating the pECG on the basis of the differentiated bio-vibration signals. In FIG. 5(B), however, in the predicted vibration pattern (the third tier from the top) on the basis of the beating vibration signals, the predicted R-waves are presented in close agreement with the R-waves in the measured ECG. In FIG. 6, the heartbeat intervals (RRIs) in the measured ECG are in good agreement with the heartbeat intervals (BBIs) in the pECG.

Conventional methods have a limited ability to determine heartbeat intervals (BBIs) from the partially irregular bio-vibration signals as obtained from Subject B under prediction illustrated in FIG. 5(A). The signal processing apparatus 20 according to the embodiments readily allows determination of the heartbeat intervals (BBIs) based on the predicted R-waves even from the said bio-vibration signals.

Figure 7A:
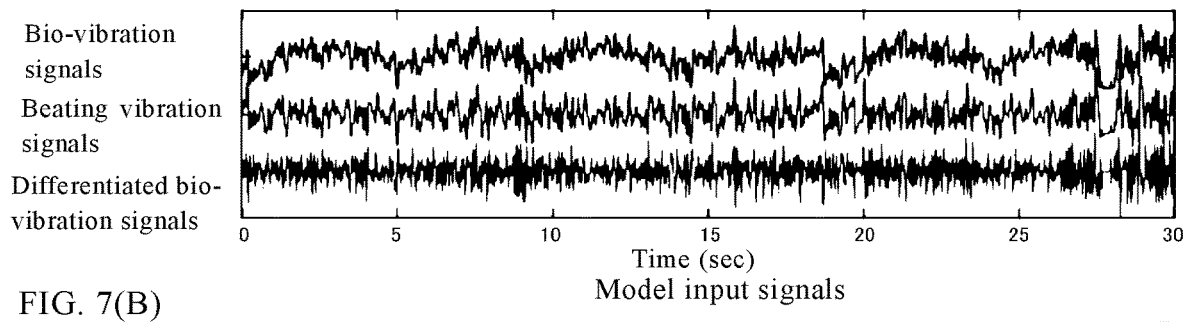
FIG. 7(A) and FIG. 7(B) The figures illustrate the model input signals of Subject C under prediction as well as the measured ECG signals and pECG signals of Subject C under prediction as waveforms.

FIG. 7(A) illustrates the model input signals of Subject C under prediction. As with FIG. 3(A), the top tier of FIG. 7(A) illustrates the bio-vibration signals as waveforms. The middle tier in FIG. 7(A) illustrates the beating vibration signals as waveforms. The bottom tier of FIG. 7(A) illustrates the differentiated bio-vibration signals as waveforms.

Figure 7B:
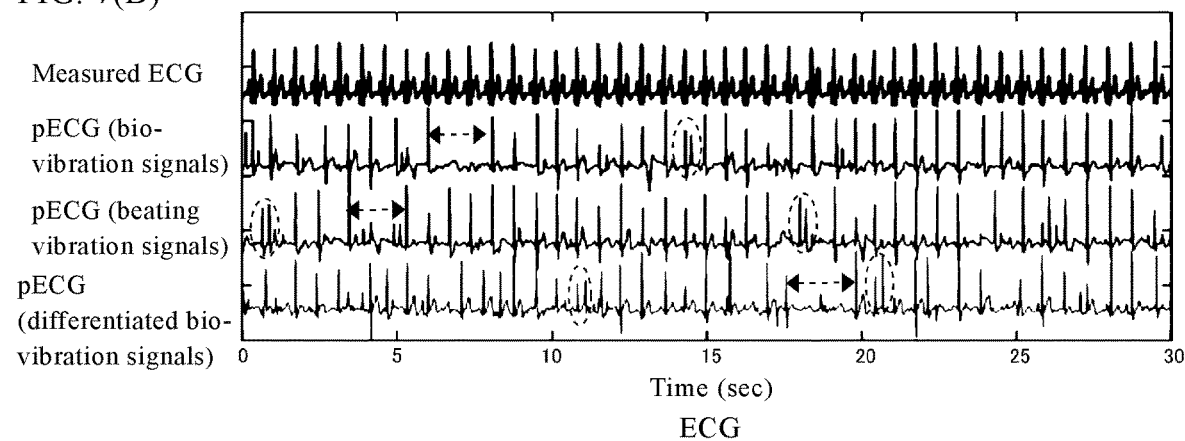

FIG. 7(B) illustrates the measured ECG signals and pECG signals of Subject C under prediction as waveforms. As with FIG. 3(B), the top tier of FIG. 7(B) illustrates the measured ECG signals as waveforms. The second tier from the top in FIG. 7(B) illustrates waveforms of the pECG signals output by the prediction model 24 on the basis of the bio-vibration signals, which are input in the prediction unit 23 as the model input signals. The third tier from the top of FIG. 7(B) illustrates waveforms of the pECG signals output by the prediction model 24 on the basis of the beating vibration signals, which are input in the prediction unit 23 as the model input signals. The bottom tier in FIG. 7(B) illustrates waveforms of the pECG signals output by the prediction model 24 on the basis of the differentiated bio-vibration signals, which are input in the prediction unit 23 as the model input signals.

Figure 8:
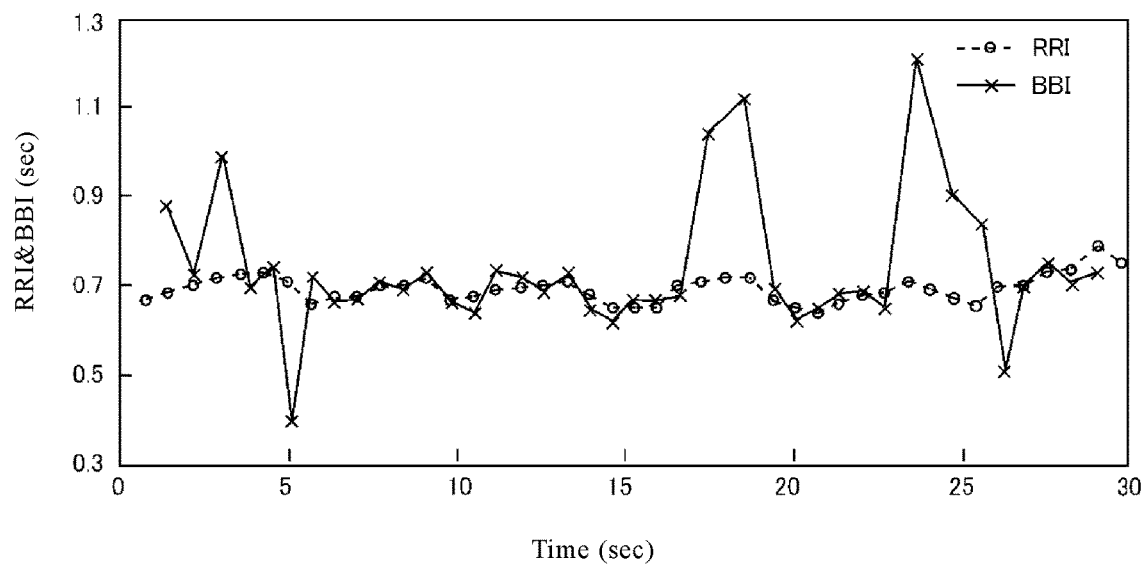
FIG. 8 The figure illustrates R-wave-based heartbeat intervals (RRIs) determined from the measured ECG signals and bio-vibration-based heartbeat intervals (BBIs) determined from the pECG on the basis of the beating vibration signals from Subject C under prediction, which are input as the model input signals.

FIG. 8 illustrates heartbeat intervals (RRIs) determined from the measured ECG signals and heartbeat intervals (BBIs) determined from the pECG on the basis of the beating vibration signals from Subject C under prediction.

In FIG. 7(B), the predicted R-wave is not presented in sections indicated with an arrow in all of 3 types of model input signals. In the sections enclosed by a broken line in all of 3 types of model input signals, 2 predicted R-waves occur adjacently. Most of the predicted R-waves in 3 types of the pECG occur almost simultaneously with the R-waves in the measured ECG.

Conventional methods have a further limited ability to determine heartbeat intervals (BBIs) from the partially irregular bio-vibration signals as obtained from Subject C under prediction illustrated in FIG. 7(A) compared with determination of the heartbeat interval (BBIs) from the bio-vibration signals as obtained from Subject B under prediction. The signal processing apparatus 20 according to the embodiments allows determination of the heartbeat intervals (BBIs) based on the predicted R-waves even from the bio-vibration signals as obtained from Subject C under prediction.

Example 2

Then, the inventors of the embodiments conducted a verification experiment using 13 humans as subjects. In this experiment, a sheet with the piezoelectric sensor 40 attached is placed on a bed mattress, and the subjects lay on the mattress in a prone, supine, left lateral, or right lateral position.

The learning unit 13 assigns the prediction model 24 to machine learning by a leave-one-out procedure. The neural network used is bidirectional LSTM (BiLSTM) neural network that transfers the learning data to a bidirectional long short-term memory layer.

Electrodes for ECG are attached to the chest of each subject to acquire ECG signals of each subject with the ECG meter 30 through bipolar leads. At the same time of acquisition of the ECG signals, bio-vibration signals from each subject who lays on a bed in the prone, supine, left lateral, or right lateral position are acquired through the piezoelectric sensor 40. A measurement time is 30 seconds for each subject.

The ECG signals acquired for 30 seconds from each of 18 subjects are normalized by taking the ratio of the deviation from the mean of all data on the ECG signals with respect to the standard deviation (each value of the ECG signals—the mean)/standard deviation). In the same manner, the ratio of the deviation from the mean of all data on the model input signals acquired for 30 seconds from each of 18 subjects with respect to the standard deviation (each value of the model input signals—the mean)/standard deviation) is determined for normalization. Then, for each subject under prediction, using the normalized model input signals and the normalized ECG signals (teaching signals) from the other 17 subjects (samples) as the training data, the prediction model 24 is generated based on the bidirectional LSTM neural network.

The model input signals are the subject's processed bio-vibration signals obtained by any of the following processes: passing through the 0.5 Hz high-pass filter; passing through the 20 Hz high-pass filter followed by absolutization; passing through the 30 Hz high-pass filter followed by absolutization; and differentiation followed by absolutization.

The normalized model input signals from the subject under prediction are input in the prediction model 24, and the prediction model 24 outputs pECG signals as the predicted ECG.

Figure 9:
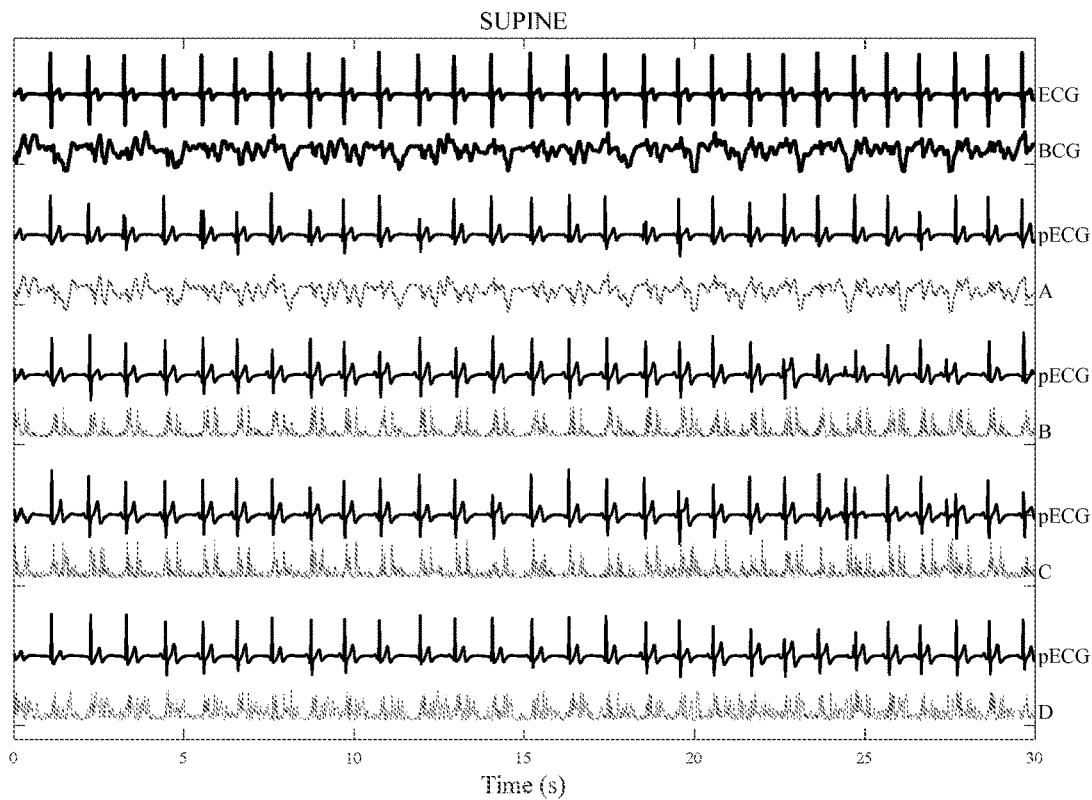
FIG. 9 The figure illustrates the measured ECG signals in a supine position, the model input signals obtained by passing the bio-vibration signals through the 0.5 Hz high-pass filter, the model input signals obtained by passing the bio-vibration signals through the 20 Hz or 30 Hz high-pass filter followed by absolutization, the model input signals obtained by differentiating the bio-vibration signals followed by absolutization, and corresponding resultant pECG signals as waveforms.

FIG. 9 illustrates the pECG and other signals obtained from a subject in the supine position.

The top tier illustrates the measured ECG signals (ECG), and the second tier from the top illustrates the bio-vibration signals (BCG) as waveforms. Tier A illustrates the model input signals obtained by passing the bio-vibration signals through the 0.5 Hz high-pass filter; Tier B illustrates the model input signals obtained by passing the bio-vibration signals through the 20 Hz high-pass filter followed by absolutization; Tier C illustrates the model input signals obtained by passing the bio-vibration signals through the 30 Hz high-pass filter followed by absolutization; and Tier D illustrates the model input signals obtained by differentiating the bio-vibration signals followed by absolutization. All the signals are illustrated as waveforms. The tier said each of the said tiers illustrating the model input signals illustrates the corresponding pECG signals output by the prediction model 24 as waveforms.

Figure 10:
FIG. 10 The figure illustrates the measured ECG signals in a prone position, the model input signals obtained by passing the bio-vibration signals through the 0.5 Hz high-pass filter, the model input signals obtained by passing the bio-vibration signals through the 20 Hz or 30 Hz high-pass filter followed by absolutization, the model input signals obtained by differentiating the bio-vibration signals followed by absolutization, and corresponding resultant pECG signals as waveforms.

FIG. 10 illustrates the pECG and other signals obtained from a subject in the prone position.

The top tier illustrates the measured ECG signals (ECG), and the second tier from the top illustrates the bio-vibration signals (BCG) as waveforms. Tier A illustrates the model input signals obtained by passing the bio-vibration signals through the 0.5 Hz high-pass filter; Tier B illustrates the model input signals obtained by passing the bio-vibration signals through the 20 Hz high-pass filter followed by absolutization; Tier C illustrates the model input signals obtained by passing the bio-vibration signals through the 30 Hz high-pass filter followed by absolutization; and Tier D illustrates the model input signals obtained by differentiating the bio-vibration signals followed by absolutization. All the signals are illustrated as waveforms. The tier said each of the said tiers illustrating the model input signals illustrates the corresponding pECG signals output by the prediction model 24 as waveforms.

Figure 11:
FIG. 11 The figure illustrates the measured ECG signals in a left lateral position, the model input signals obtained by passing the bio-vibration signals through the 0.5 Hz high-pass filter, the model input signals obtained by passing the bio-vibration signals through the 20 Hz or 30 Hz high-pass filter followed by absolutization, the model input signals obtained by differentiating the bio-vibration signals followed by absolutization, and corresponding resultant pECG signals as waveforms.

FIG. 11 illustrates the pECG and other signals obtained from a subject in the left lateral position.

The top tier illustrates the measured ECG signals (ECG), and the second tier from the top illustrates the bio-vibration signals (BCG) as waveforms. Tier A illustrates the model input signals obtained by passing the bio-vibration signals through the 0.5 Hz high-pass filter; Tier B illustrates the model input signals obtained by passing the bio-vibration signals through the 20 Hz high-pass filter followed by absolutization; Tier C illustrates the model input signals obtained by passing the bio-vibration signals through the 30 Hz high-pass filter followed by absolutization; and Tier D illustrates the model input signals obtained by differentiating the bio-vibration signals followed by absolutization. All the signals are illustrated as waveforms. The tier said each of the said tiers illustrating the model input signals illustrates the corresponding pECG signals output by the prediction model 24 as waveforms.

Figure 12:
FIG. 12 The figure illustrates the measured ECG signals in a right lateral position, the model input signals obtained by passing the bio-vibration signals through the 0.5 Hz high-pass filter, the model input signals obtained by passing the bio-vibration signals through the 20 Hz or 30 Hz high-pass filter followed by absolutization, the model input signals obtained by differentiating the bio-vibration signals followed by absolutization, and corresponding resultant pECG signals as waveforms.

FIG. 12 illustrates the pECG and other signals obtained from a subject in the right lateral position.

The top tier illustrates the measured ECG signals (ECG), and the second tier from the top illustrates the bio-vibration signals (BCG) as waveforms. Tier A illustrates the model input signals obtained by passing the bio-vibration signals through the 0.5 Hz high-pass filter; Tier B illustrates the model input signals obtained by passing the bio-vibration signals through the 20 Hz high-pass filter followed by absolutization; Tier C illustrates the model input signals obtained by passing the bio-vibration signals through the 30 Hz high-pass filter followed by absolutization; and Tier D illustrates the model input signals obtained by differentiating the bio-vibration signals followed by absolutization. All the signals are illustrated as waveforms. The tier said each of the said tiers illustrating the model input signals illustrates the corresponding pECG signals output by the prediction model 24 as waveforms.

Figure 13:
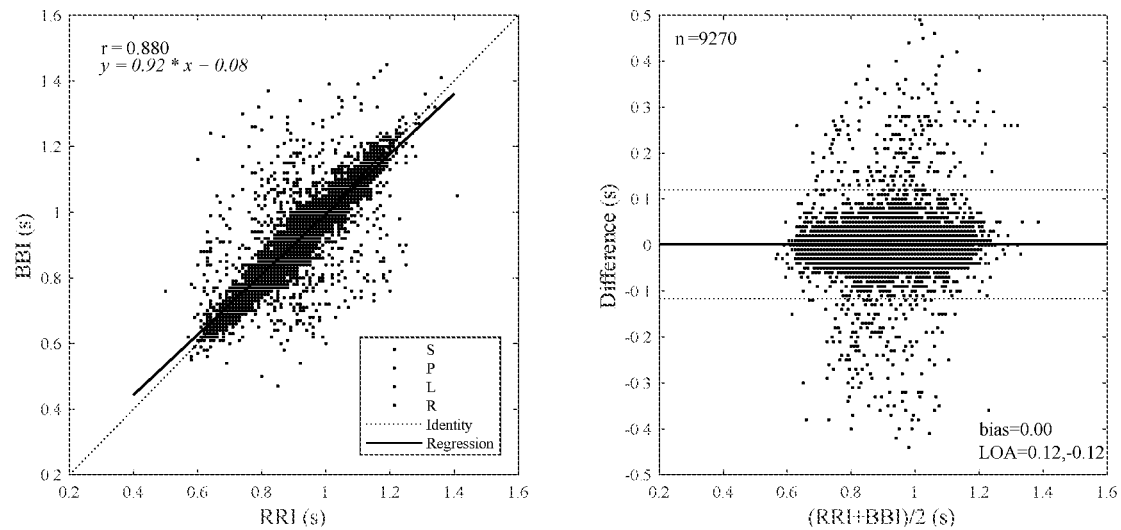
FIG. 13 The figure illustrates a Bland-Altman Plot between the heartbeat intervals (BBIs) determined from the pECG on the basis of the model input signals obtained by passing the bio-vibration signals in the prone, supine, left lateral, or right lateral position through the 30-Hz high-pass filter followed by absolutization and the RRIs determined from the measured ECG.

FIG. 13 illustrates a Bland-Altman Plot between the heartbeat intervals (BBIs) determined from the pECG on the basis of the model input signals obtained by the 30-Hz high-pass filtration and absolutization and the RRIs determined from the measured ECG using data presented in FIGS. 9 to 12. As illustrated, the RRIs determined from the measured ECG favorably agree with the BBIs determined from the predicted ECG, hardly involving systematic errors.

As described said, when the absolutized high-frequency component of the beating vibration signals obtained by passing the bio-vibration signals through the 30 Hz high-pass filter are used as the model input signals in the learning unit 13 and prediction unit 23, the resultant pECG signals highly agree with the measured ECG signals in any of the prone, supine, left lateral, and right lateral positions.

Figure 14:
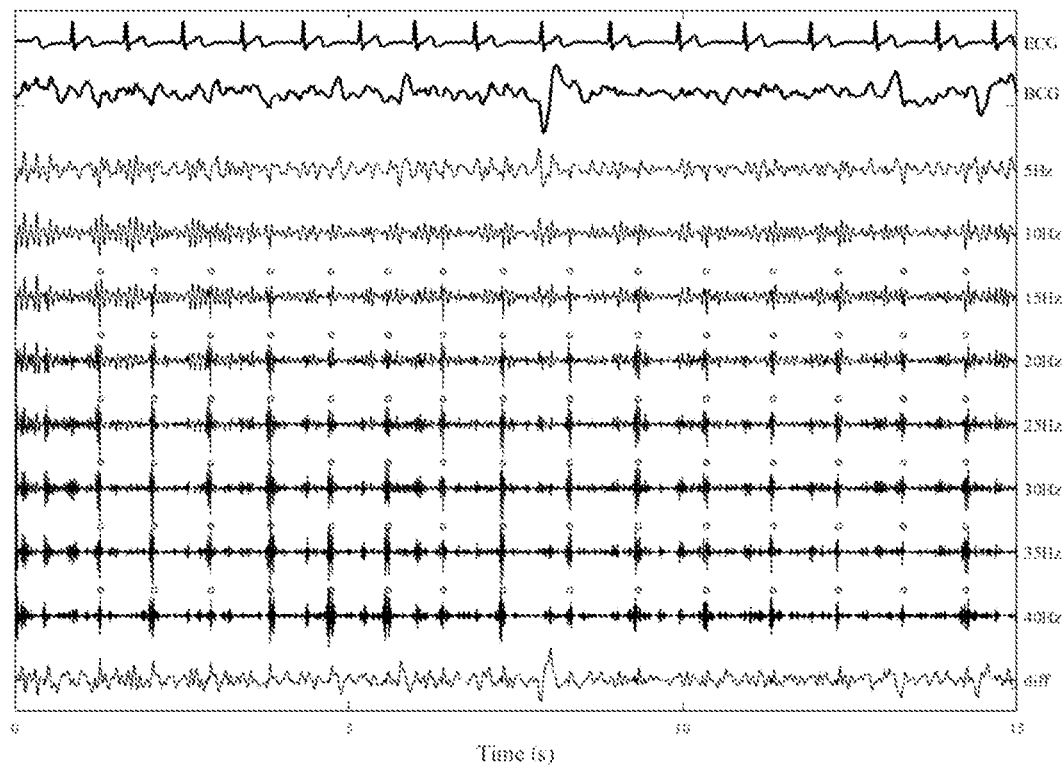
FIG. 14 The figure illustrates the measured ECG signals, bio-vibration signals, filtered bio-vibration signals obtained by passing the 5 Hz, 10 Hz, 15 Hz, 20 Hz, 25 Hz, 30 Hz, 35 Hz, or 40 Hz high-pass filter, and differentiated bio-vibration signals as waveforms.

FIG. 14 illustrates the measured ECG signals (ECG) in the prone position, the bio-vibration signals (BCG), and the filtered bio-vibration signals obtained by passing through the 5 Hz, 10 Hz, 15 Hz, 20 Hz, 25 Hz, 30 Hz, 35 Hz, or 40 Hz high-pass filter, and the differentiated bio-vibration signals (diff) as waveforms. In the waveforms of the filtered bio-vibration signals obtained by passing through high-pass filters with the cutoff frequency of 20 Hz and higher in FIG. 14, a heart sound of large amplitude indicated with an open circle appears at a position just after that of a T-wave in the measured ECG signals.

Comparison of the said waveforms with FIGS. 9 to 12 leads to a finding that favorable waveforms of the pECG signals are obtained when prediction is performed after the model input signals obtained by passing the bio-vibration signals through the 20 Hz to 30 Hz high-pass filter followed by absolutization are used for learning.

Figure 15:
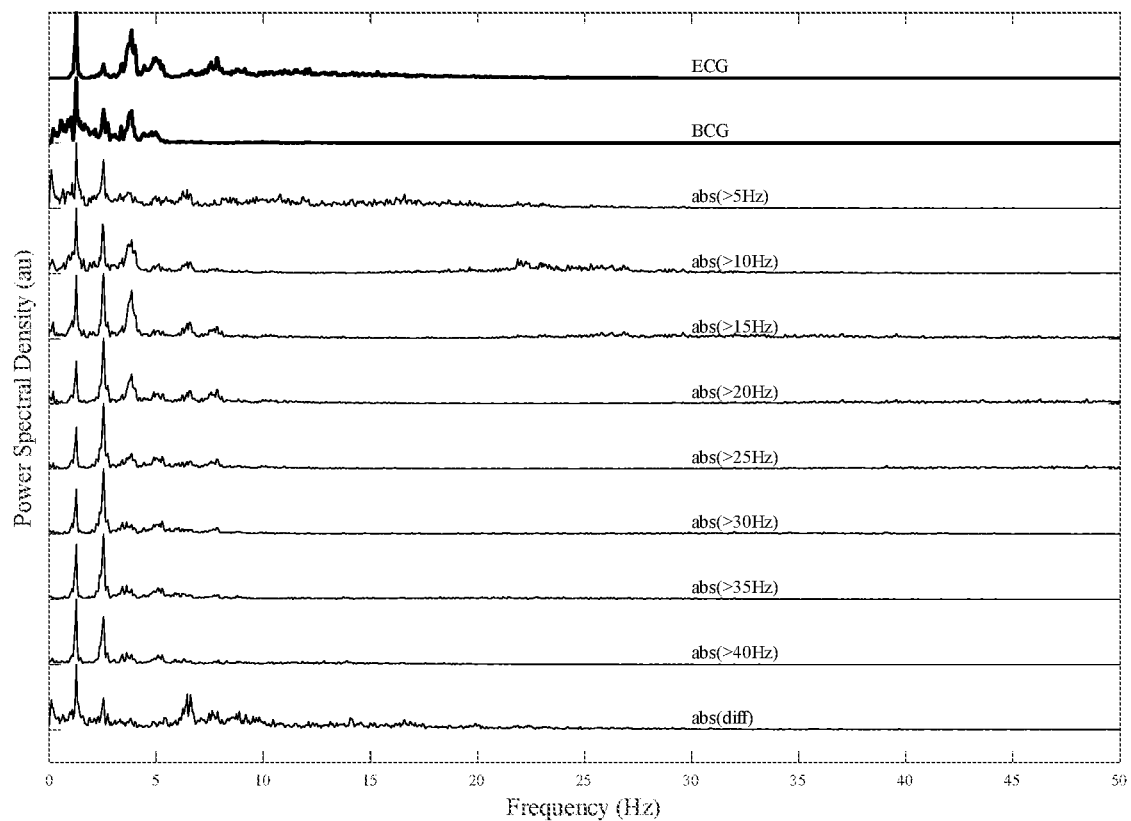
FIG. 15 The figure illustrates power spectra of data in FIG. 14.

FIG. 15 illustrates power spectra derived from data in FIG. 14, which present the fundamental frequency of the heartbeat (in a neighborhood of 1 Hz), the first harmonic, and the second harmonic.

The heart sound signals observed with the high-pass filters with the cutoff frequency of 20 Hz and higher in FIG. 14 are also obtained with a phonocardiograph.

Example 3

The inventors of the embodiments conducted a verification experiment in 3 human subjects using a fingertip piezoelectric sphygmometer as the piezoelectric sensor. The learning unit 13 assigns the prediction model 24 to machine learning by a leave-one-out procedure. The neural network used is bidirectional LSTM (BiLSTM) neural network that transfers the learning data to a bidirectional long short-term memory layer.

The ECG meter 30 is connected with the chest of each subject through bipolar leads to acquire the ECG signals. At the same time of acquisition of the ECG signals, bio-vibration signals from the subject are acquired with the piezoelectric sphygmometer, which is attached to his or her fingertip as the piezoelectric sensor 40. A measurement time is 30 seconds for each subject.

The ECG signals acquired for 30 seconds from each subject are normalized by taking the ratio of the deviation from the mean of all data on the ECG signals with respect to the standard deviation (each value of the ECG signals—the mean)/standard deviation). In the same manner, the ratio of the deviation from the mean of all data on the model input signals acquired for 30 seconds from each subject with respect to the standard deviation (each value of the model input signals—the mean)/standard deviation) is determined for normalization.

Then, for each subject under prediction, using the normalized model input signals and the normalized ECG signals (teaching signals) from the other subjects (samples) as the training data, the prediction model 24 is generated based on the bidirectional LSTM neural network.

The model input signals are the bio-vibration signals obtained from the subject. The normalized model input signals from the subject under prediction are input in the prediction model 24, and the prediction model 24 outputs pECG signals as the predicted ECG.

Figure 16A:
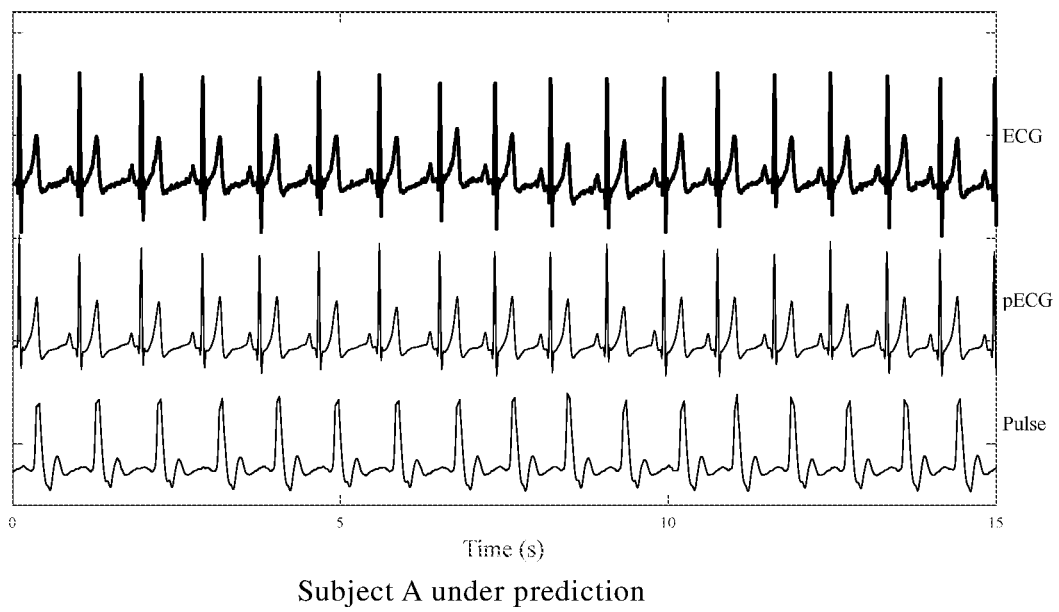
FIG. 16(A), FIG. 16(B), and FIG. 16(C) The figures illustrate the measured ECG signals, model input signals, and pECG signals in 3 subjects (Subject A under prediction, Subject B under prediction, and Subject C under prediction) in whom the fingertip piezoelectric sphygmometer is used as the piezoelectric sensor.
Figure 16B:
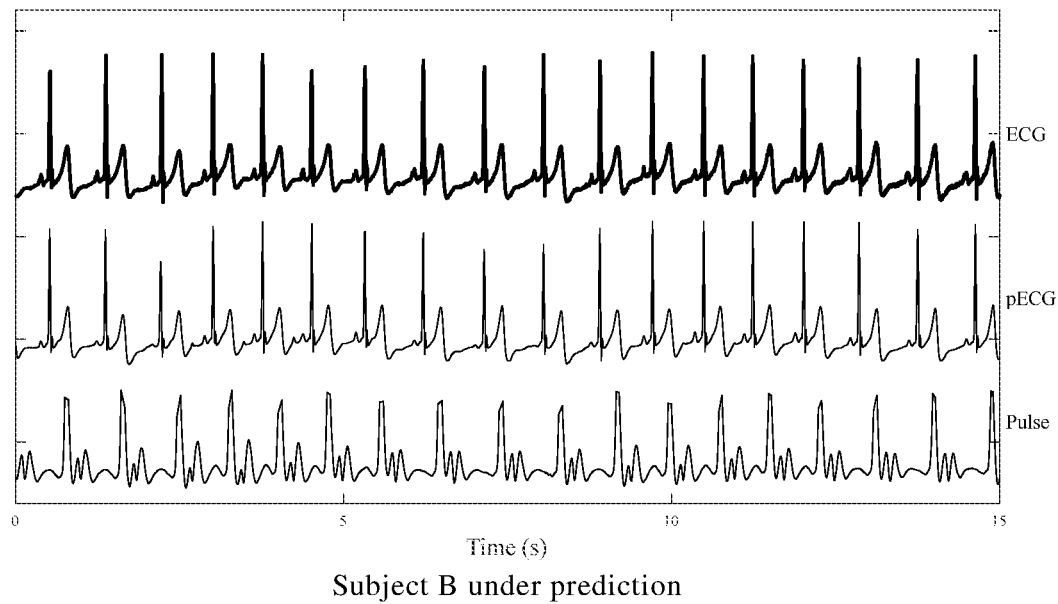
Figure 16C:
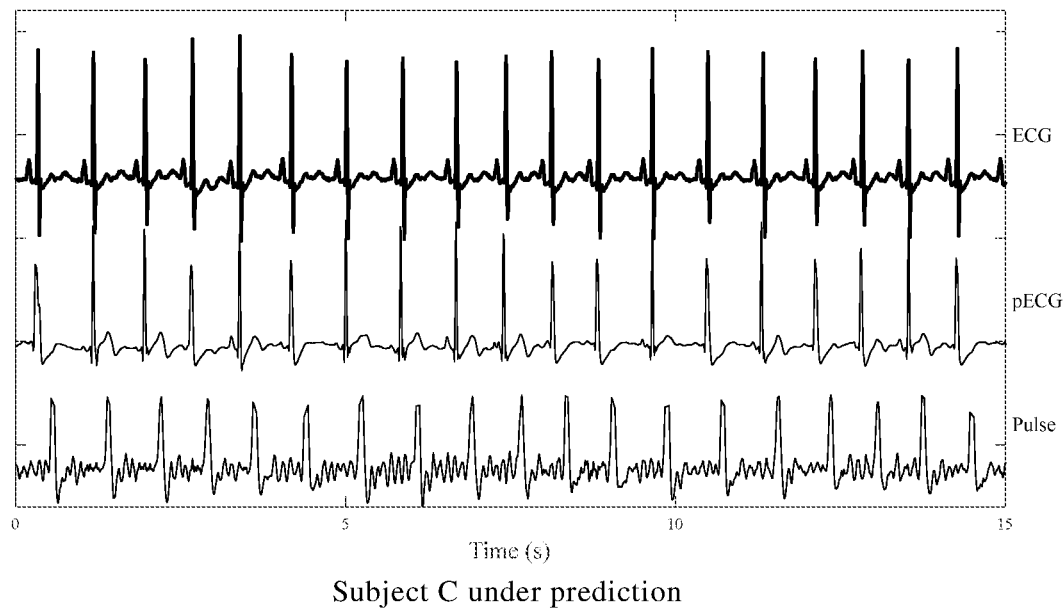

FIG. 16(A), FIG. 16(B), and FIG. 16(C) illustrate the pECG signals and other signals from Subject A under prediction, Subject B under prediction, and Subject C under prediction.

The top tiers of FIG. 16(A), FIG. 16(B), and FIG. 16(C) illustrate the measured ECG signals (ECG).

The bottom tiers of FIG. 16(A), FIG. 16(B), and FIG. 16(C) illustrate the bio-vibration signals (Pulse) acquired with the piezoelectric sphygmometer, which are clear and thus directly normalized to obtain the model input signals as waveforms.

The middle tiers of FIG. 16(A), FIG. 16(B), and FIG. 16(C) illustrate the pECG signals (pECG) output by the prediction model 24 on basis of the said bio-vibration signals themselves as waveforms.

In addition, a photoplethysmographic sensor provides the bio-vibration signals in clear waveforms comparable to the waveforms of the bio-vibration signals (Pulse) acquired with the fingertip piezoelectric sphygmometer presented in the bottom tiers of FIG. 16(A), FIG. 16(B) and FIG. 16(C), yielding the pECG signals in favorable waveforms.

In this verification experiment, the bio-vibration signals are acquired with the piezoelectric sensor attached on the buttock. The beating vibrations included in the bio-vibration signals on the buttock are aggregates of pressure pulse waves transmitted from the heart to the buttock tissue through arterial blood vessels and deemed as signals vibrating up and down in response to an arterial blood pressure gradient between an ascending aorta and a descending aorta. In addition, the beating vibrations included in the bio-vibration signals on the buttock are deemed to be weaker than the original beating vibrations owing to absorption of the pressure pulse waves in body tissues. This verification experiment demonstrates that even from the bio-vibration signals in disturbed waveforms as illustrated in FIG. 3(A), FIG. 5(A), and FIG. 7(A), heartbeat intervals (BBIs) are obtained.

The model input signals obtained by the processing described below are demonstrated to derive favorable pECG signals in any of the prone, supine, left lateral, and right lateral positions as illustrated in FIGS. 9, 10, 11, and 12. In the processing, the bio-vibration signals are passed through the high-pass filter with the cutoff frequency of 20 Hz to 30 Hz, and of the obtained beating vibration signals, the high-frequency component is absolutized to obtain signals presenting heart sounds as the model input signals.

In view of FIG. 14, the cutoff frequency of the high-pass filter may not have to be strictly 20 Hz to 30 Hz as long as the heart sounds are presented.

With the piezoelectric sensor 40, when operating as the piezoelectric sphygmometer, the clear bio-vibration signals are obtained and thus directly used as the model input signals, yielding favorable pECG signals.

The said EXAMPLES have limitations in terms of the number of subjects (samples) and time for acquisition of the bio-vibration signals. The increased number of subjects (samples) and extended time for acquisition of the bio-vibration signals (leading to generation of big data) is expected to improve the accuracy of prediction with the prediction model established on the basis of resultant expanded data, allowing the waveforms of the pECG to approach to the waveforms of the measured ECG.

In addition, the prediction model dedicated to an individual may be established using the same individual as both the sample and subject under prediction.

Furthermore, the prediction models may be established according to a physical condition such as gender, age, body height or sitting height, body weight, obesity index, or other parameters.

In the case where the piezoelectric sensor is placed on the seat of a chair to acquire the bio-vibration signals on the buttock, the prediction model established according to the sitting height is expected to improve the accuracy of the prediction, allowing the waveforms of the pECG to approach to the waveforms of the measured ECG, because humans of similar sitting heights mostly have a similar distance between the heart and buttock as well.

In addition, separate prediction models may be established according to a place of the piezoelectric sensor such as the seat of a chair, under and on the bedding including bed mattress and futon, or other surfaces.

Furthermore, separate prediction models may be established according to a human body site of the piezoelectric sensor attached such as wrist, arm, foot, temple, or other positions.

In addition, the said description of the embodiments covers the piezoelectric sensor that uses the sheet-type piezoelectric element made of polyvinylidene difluoride (PVDF), but the embodiments can be implemented by the other piezoelectric sensor as long as the sensor detects the bio-vibration signals.

For example, piezoelectric sensors that use the piezoelectric element made of a piezoelectric polymer material (polyolefin materials) can implement the embodiments. The material for the piezoelectric element may be, for example, porous polypropylene electret film (electro mechanical film, EMFI), poly[(vinylidenefluoride-co-trifluoroethylene] (P(VDF-TrFE), or poly[(vinylidenefluoride-co-tetrafluoroethylene] (P(VDF-TFE)). The piezoelectric sensor that uses the piezoelectric element made of any of the said materials can implement the embodiments.

Furthermore, accelerometry sensors can implement the embodiments.

Volume pulse waves measured with the photoplethysmograph can also lead to implementation of the embodiments.

Specifically, the accelerometry sensors and photoplethysmographic sensors are examples of bio-vibration signal acquisition apparatuses of the embodiments, and vibrations derived from the volume pulse waves acquired with the photoplethysmograph are an example of beating vibrations described in the embodiments.

In addition, for example, the phonocardiograph can implement the embodiments.

As described said, according to the embodiments, the phonocardiograph measures the bio-vibration signals that include vibrations derived from heartbeats, are equivalent to the ECG signals, and at least contain a component delivering the predicted R-waves. The phonocardiograph, therefore, acquires signals that are readily turned into the heartbeat interval or heart rate.

In addition, there are ongoing various trials to predict blood pressure on the basis of waveforms of the ballistocardiac movements and waveforms of the pulse waves. In the blood pressure prediction as described said, the heartbeat interval and pulse arrival time (PAT) are important parameters. The heartbeat interval can be determined from the pECG. In addition, the PAT can be determined from time of the predicted R-wave and time of a rising of the beating vibration signals. According to the embodiments, 1 piezoelectric sensor or 1 photoplethysmographic sensor placed at a site distant from the heart to a certain extent can achieve the blood pressure prediction.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

REFERENCE SIGNS LIST

1. Signal processing system, 10. Prediction modeling apparatus, 11. Input unit, 12. Preprocessing unit, 13. Learning unit, 20. Signal processing apparatus, 21. Input unit, 22. Preprocessing unit, 23. Prediction unit, 24. Prediction model, 25. Post-processing unit, 26. Output unit, 30. ECG meter, and 40. Piezoelectric sensor

The invention claimed is:

1. A signal processing apparatus, comprising:
a learning unit configured to
receive ECG signals of a sample acquired with an ECG meter and ballistocardiac movement signals of the sample which are acquired with a piezoelectric sensor simultaneously with the ECG signals of the sample and include beating vibration signals derived from heartbeats of the sample, and
generate a prediction model through machine learning in which the ECG signals of the sample are determined as teaching data, and model input signals of the sample are obtained as inputs by performing a predetermined processing on the ballistocardiac movement signals of the sample; and
a prediction unit configured to
receive the prediction model from the learning unit, and
output pECG signals predicted by the prediction model upon input of model input signals of a prediction subject obtained by performing the predetermined processing on ballistocardiac movement signals of the prediction subject which are acquired with the piezoelectric sensor.

2. The signal processing apparatus according to claim 1, wherein the model input signals are one of differentiated signals of the ballistocardiac movement signals, beating vibration signals extracted from the ballistocardiac movement signals, and differentiated signals of the beating vibration signals, or absolutized signals thereof.

3. The signal processing apparatus according to claim 1, wherein the predetermined processing performs one of following initial procedures in which the ballistocardiac movement signals are passed through a high-pass filter with a cutoff frequency of 0.5 Hz, in which the ballistocardiac movement signals are passed through a high-pass filter with a cutoff frequency for extraction of heart sound signals, and in which the ballistocardiac movement signals are passed through a band-pass filter (BPF) with a pass-band of 0.5 Hz to 40 Hz, and then performs at least one of differentiation and absolutization on signals passed through the initial procedures, and thereafter performs final normalization on signals calculated through the at least one of differentiation and absolutization.

4. The signal processing apparatus according to claim 3, wherein the cutoff frequency of the high-pass filter is 20 Hz to 40 Hz.

5. The signal processing apparatus according to claim 1, further comprising
a post-processing unit configured to
determine heartbeat intervals on a basis of the pECG signals output from the prediction unit, and
eliminate a part of heartbeat data involving an outlying heartbeat interval if the outlying heartbeat interval is found.

6. The signal processing apparatus according to claim 1, wherein the piezoelectric sensor is a sheet piezoelectric sensor.

7. A system for signal processing, comprising:
the signal processing apparatus according to claim 1;
the ECG meter that acquires the ECG signals of the sample;
the piezoelectric sensor that acquires the ballistocardiac movement signals of the sample and the prediction subject; and
a prediction modeling apparatus provided with the learning unit that generates the prediction model by the machine learning.

8. The signal processing apparatus according to claim 1, wherein the machine learning is performed with bidirectional LSTM (BiLSTM) neural network.

9. A non-transitory tangible computer-readable storage media storing computer-executable instructions for signal processing, the instructions comprising:
generating a prediction model by machine learning in which ECG signals of a sample acquired with an ECG meter are determined as teaching data, and model input signals of the sample are obtained as inputs by performing a predetermined processing on the ballistocardiac movement signals of the sample which are acquired with a piezoelectric sensor simultaneously with the ECG signals and include beating vibration signals derived from heartbeats of the sample; and
outputting pECG signals predicted by the prediction model upon input of model input signals of a prediction subject obtained by performing the predetermined processing on ballistocardiac movement signals of the prediction which are acquired with the piezoelectric sensor.

* * * * *